United States Patent
Tian

[19]

[11] Patent Number: 6,093,208
[45] Date of Patent: Jul. 25, 2000

[54] ANTILUXATION HIP PROSTHESIS

[76] Inventor: Enrico Tian, Via Scalone Castel San Pietro, 7, 37126 Verona, Italy

[21] Appl. No.: 09/307,607

[22] Filed: May 10, 1999

[30] Foreign Application Priority Data

May 12, 1998 [IT] Italy ................................ VR980029 U

[51] Int. Cl.[7] ...................................................... A61F 2/34
[52] U.S. Cl. ................. 623/22.2; 623/22.24; 623/22.29; 623/22.17
[58] Field of Search .................. 623/19, 18, 22, 623/23, 22.15, 22.17, 22.18, 22.2, 22.21, 22.24, 22.27, 22.28, 22.29

[56] References Cited

U.S. PATENT DOCUMENTS

| | | | |
|---|---|---|---|
| 3,818,512 | 6/1974 | Shersher | 623/22 |
| 4,795,471 | 1/1989 | Oh | 623/23 |
| 4,798,610 | 1/1989 | Averill et al. | 623/22 |
| 5,019,105 | 5/1991 | Wiley | 623/22 |
| 5,062,853 | 11/1991 | Forte | 623/22 |
| 5,092,898 | 3/1992 | Bekki et al. | 623/22 |
| 5,263,988 | 11/1993 | Huebner | 623/22 |
| 5,314,491 | 5/1994 | Thongpreda et al. | 623/22 |
| 5,458,649 | 10/1995 | Spotorno et al. | 623/22 |
| 5,755,807 | 5/1998 | Anstaett et al. | 623/23 |

*Primary Examiner*—Jeffrey A. Smith
*Assistant Examiner*—Eduardo C. Robert
*Attorney, Agent, or Firm*—Guido Modiano; Albert Josif; Daniel O'Byrne

[57] ABSTRACT

An antiluxation hip prosthesis (1) has: a hollow ring nut (2) which can be secured to the pelvis and delimits a receiving seat (2a); a cotyloid cavity or acetabular insert (3) which can be accommodated in the receiving seat and delimits a substantially hemispherical seat (3a); a spherical head (4) of an artificial femur which can be located in the seat of the cotyloid cavity; and a flange (5) which can be inserted onto the artificial femur to abut against the spherical head and rigidity coupled to the cotyloid cavity to keep the spherical head permanently in the seat so that it is free to perform articulated movements. The flange has a central hole with a concave radiused surface (21) which in use engages the spherical head. The flange is screwable about a cylindrical portion of the cotyloid cavity to mutually couple the flange to the cotyloid cavity. Alternatively, the flange and, cotyloid cavity are mutually coupled by a bayonet coupling.

8 Claims, 5 Drawing Sheets

ANTILUXATION HIP PROSTHESIS

BACKGROUND OF THE INVENTION

The present invention relates to an antiluxation hip prosthesis particularly for patients who have suffered irreversible bone traumas in the femoral region or degenerative disorders affecting said region.

A hip prosthesis usually involves reconstructing the cotyloid cavity by means of an acetabular cup, which is fixed to the pelvis and in which an acetabular insert is located to contain an artificial femoral head which can be secured to the femoral shaft so as to restore the coxofemoral joint.

The head is usually kept in correct working position in the acetabular insert solely by the action of muscle fibers that particularly under stress or in case of sudden broad movements are unable to prevent luxations, which entail either surgical operation for reinsertion and retention of the head in its seat or, after noninvasive reduction of the luxation, prolonged immobilization with plaster casts or orthopedic tutors which are often insufficient or cause general or local problems to the patient.

SUMMARY OF THE INVENTION

The main object of the present invention is to provide a hip prosthesis which is capable of ensuring permanent retention of a head in the cotyloid cavity and thus avoiding luxations.

Another object of the present invention is to provide a hip prosthesis which is relatively easy and inexpensive to manufacture and highly reliable in use.

These and other objects which will become better apparent hereinafter are achieved by a hip prosthesis having:

a hollow ring nut which can be secured to the pelvis and delimits a receiving seat;

a cotyloid cavity which can be accommodated in said receiving seat and delimits a substantially hemispherical acetabular seat or insert; and a spherical head of an artificial femur which can be located in said acetabular seat of said cotyloid cavity and comprises a flange which can be inserted onto said femur to abut against its spherical head and rigidly coupled to said cotyloid cavity or insert to keep said artificial head permanently in said seat so that it is free to perform articulated movements therein.

BRIEF DESCRIPTION OF THE DRAWINGS

The invention is further described hereinafter with reference to the accompanying drawings, wherein.

In the accompanying drawings, identical or similar parts or components have been designated by the same reference numerals.

DESCRIPTION OF THE PREFERRED EMBODIMENTS

Figure 1:
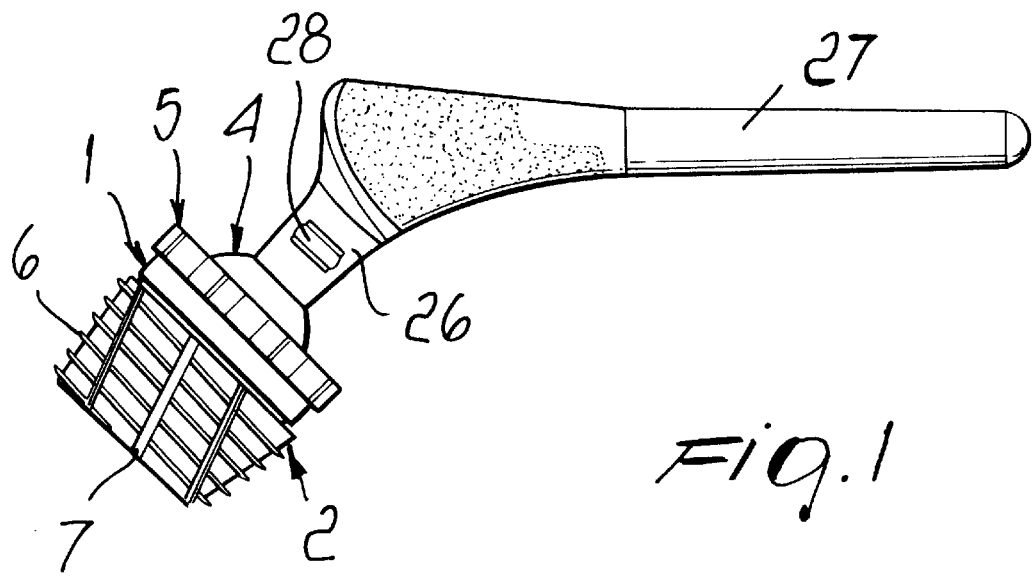
FIG. 1 is a side elevation view of a prosthesis according to the invention, complete with a femoral shaft.
Figure 2:
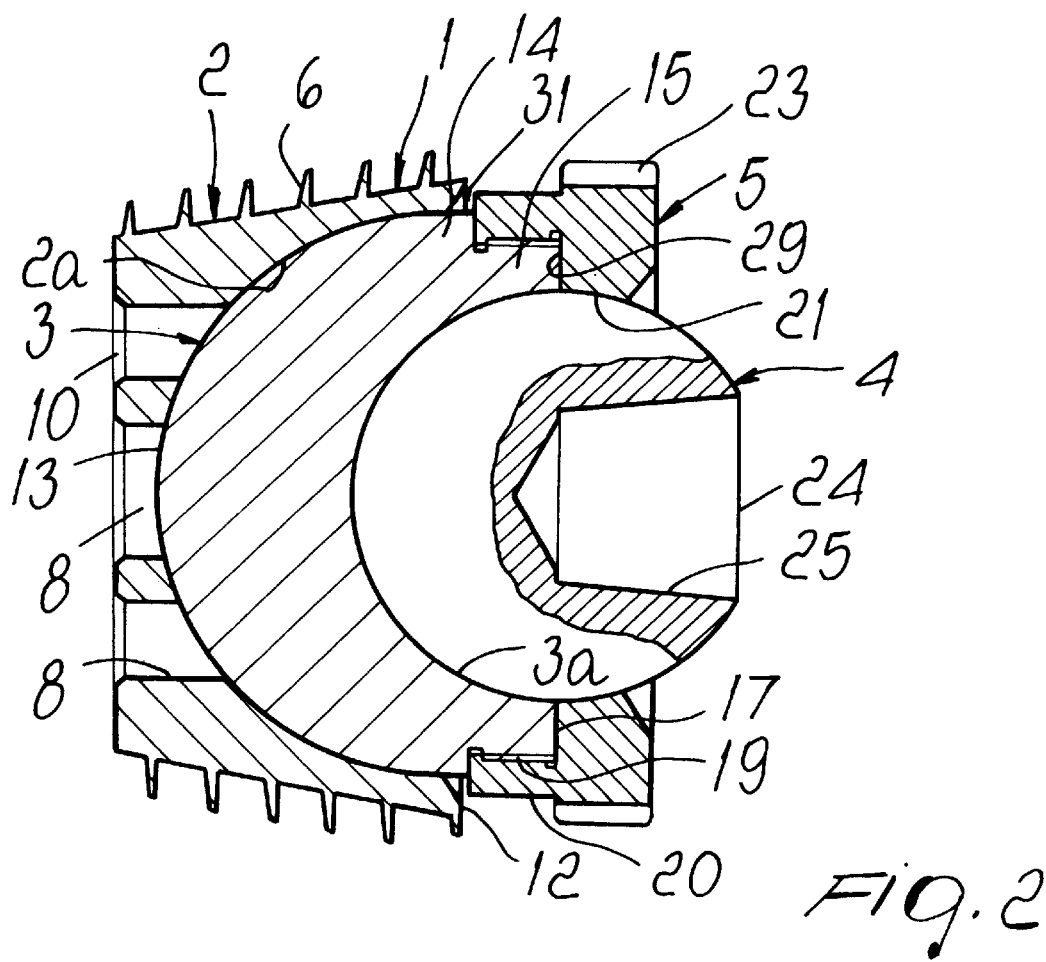
FIG. 2 is an enlarged-scale sectional view of a prosthesis according to the invention, with parts removed.

With reference first to FIGS. 1 and 2, it will be seen that a prosthesis according to the invention, generally designated by the reference numeral 1, is formed by;

a hollow ring nut 2, which can be implanted in the pelvis and delimits a hemispherical receiving seat 2a;

a cotyloid cavity or acetabular insert 3, which can be located in the receiving seat 2a of the ring nut and delimits a substantially hemispherical seat 3a;

an artificial spherical head 4 of a femur, which is arranged to fit in the seat 3a and perform articulated angular movements with respect to said seat; and a flange 5, which can be rigidly coupled to the cotyloid cavity or insert 3 and is arranged to retain the artificial head 4 inside said cavity or insert so that said head can freely rotate.

The ring nut 2 can be of any suitable type, e.g., it has an external frustum-shaped configuration with fins or threads 6 for being anchored to the pelvis of the patient, which are interrupted along straight but oblique transverse portions 7 (FIG. 2), or it can have a hemispherical non-threaded external surface to be secured to the pelvis by press-fit, with or without additional anchorings by means of protruding screws or pins.

Figure 3:
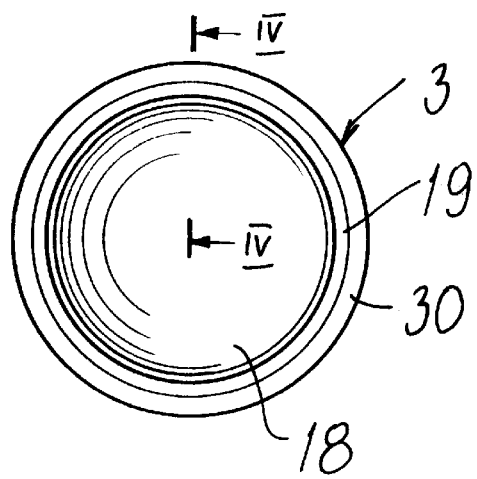
FIG. 3 is a view, taken from below or from the concave part, of a cotyloid cavity.
Figure 4:
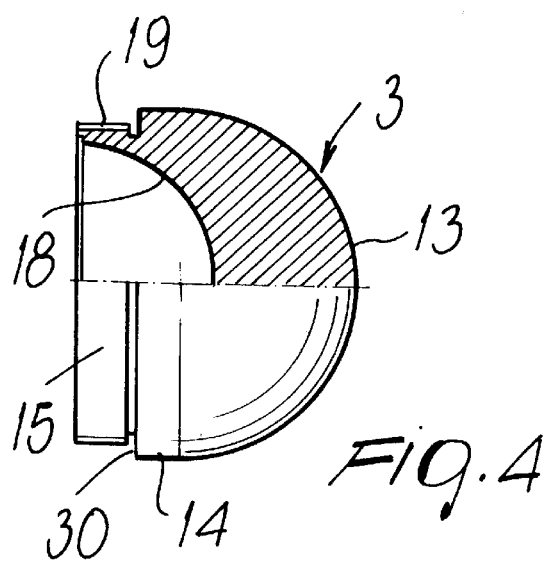
FIG. 4 is a partially cross-sectional side view, taken along the line IV—IV of FIG. 3.

Said ring nut is internally provided with the hemispherical receiving seat 2a, whose bottom or smaller end face 10 is formed with through holes 8. The cotyloid cavity or insert 3 is located in the receptacle 2a, externally constitutes (FIGS. 3 and 4) a hemispherical dome 13 whose radius is equal to, or slightly smaller than, that of the receiving seat 2a, and terminates with a cylindrical portion 14 which, in use, protrudes from the ring nut 2. The cylindrical portion 14 is designed to prevent angular movements of the cotyloid cavity or insert 3 once it has been seated in the receiving seat 2a.

Figure 5:
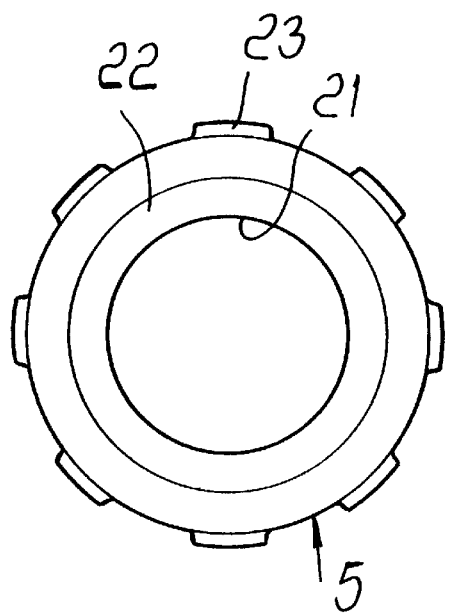
FIG. 5 is a reduced-scale top view of the flange of the prosthesis of FIG. 2.
Figure 6:
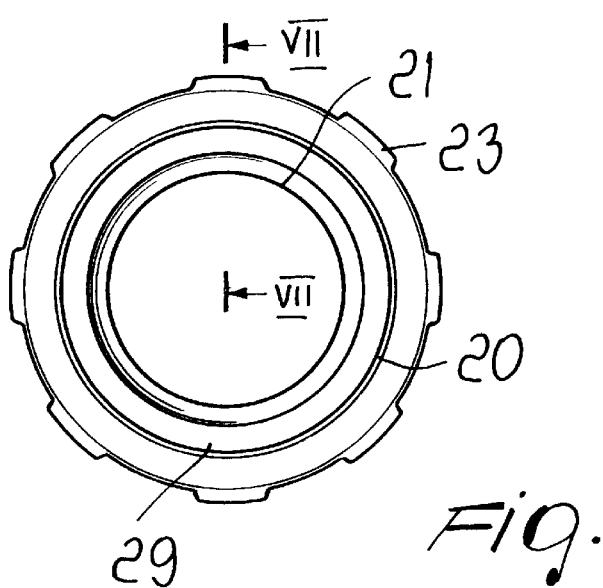
FIG. 6 is a bottom view of the flange of FIG. 5.
Figure 7:
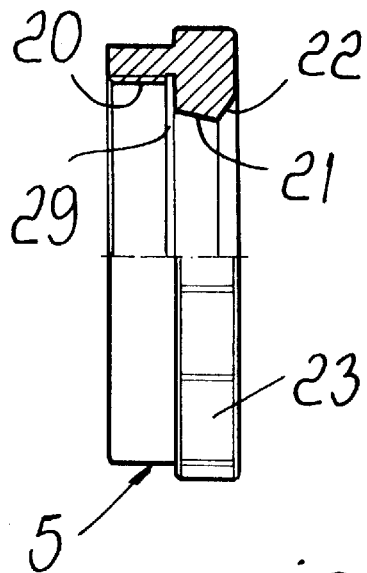
FIG. 7 is a partially cross-sectional side view taken along the line VII—VII of FIG. 6.

The cylindrical portion 14 of the cotyloid cavity or insert 3 delimits, at its outer face 17, the hemispherical chamber or seat 3a which is arranged to receive therein the artificial head 4 of the femur. Moreover, outside the seat 3a, the portion 14 has a threaded region 19 onto which an internally threaded collar 20 of the flange 5 can be screwed. More particularly, with reference to FIGS. 5 to 7, the flange 5 has a central hole 21 with a radius ed surface which is concave toward the inside, i.e., toward the femoral head 4, and a flared surface 22 which extends outwards. The flange 5 also has an external toothed ring 23 for safe grip and easy handling during assembly and screwing onto the cotyloid cavity 3.

Figure 8:
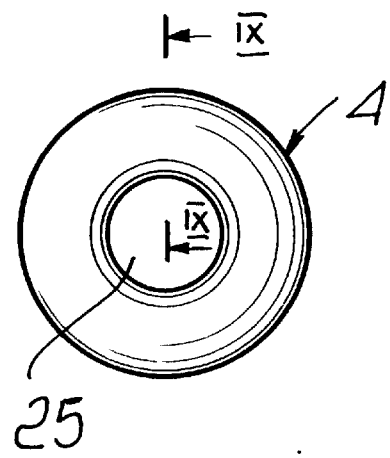
FIG. 8 is a reduced-scale view, taken from below, of the artificial femoral head of FIG. 2.
Figure 9:
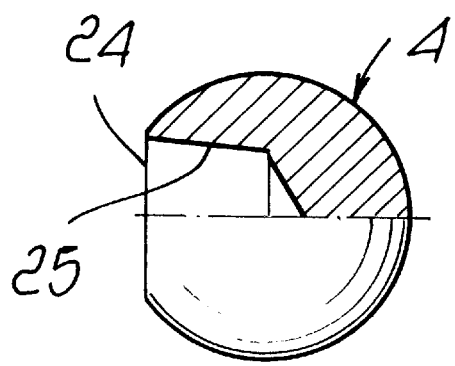
FIG. 9 is a partially cross-sectional side view, taken along the line IX—IX of FIG. 8.

FIGS. 8 and 9 show that the femoral head 4 is substantially spherical in shape and has one flat region 24 which, in use, is facing outwards and protrudes from the flange 5. A frustum-shaped dead hole 25 is formed in said flat region 24 and is arranged to receive a tubular anchoring tab 26 of a femoral pin 27 (FIG. 2).

The steps for fitting the prosthesis 1 are as follows:
securing the ring 2 to the pelvis;
preparing the cotyloid cavity or insert 3 and inserting it into the ring nut 2;
preparing the femoral pin 27 without the head 4;
placing the flange 5 on the neck of the femoral shaft 27;
fixing the head 4 to the femoral shaft 27;
inserting the femoral head 4 into the receiving seat 3a of the cotyloid cavity 3;
screwing the flange 5 onto the cotyloid cavity 3 so that radiused concave surface 21 fits against the head 4, thereby allowing articulated rotations of said head 4 but preventing it from escaping from the seat 3a and thus avoiding luxations.

After assembly, it will be noted (FIG. 1) that the flange 5 accommodates most of the cylindrical portion of the cotyloid cavity 3 and can abut against the adjacent edge 12 of the ring nut 2. Preferably, a slight clearance 31 remains between the flange 5 and the ring nut 2 since the cylindrical portion 14 of the cotyloid cavity 3 protrudes beyond the ring nut 2.

Figure 10:
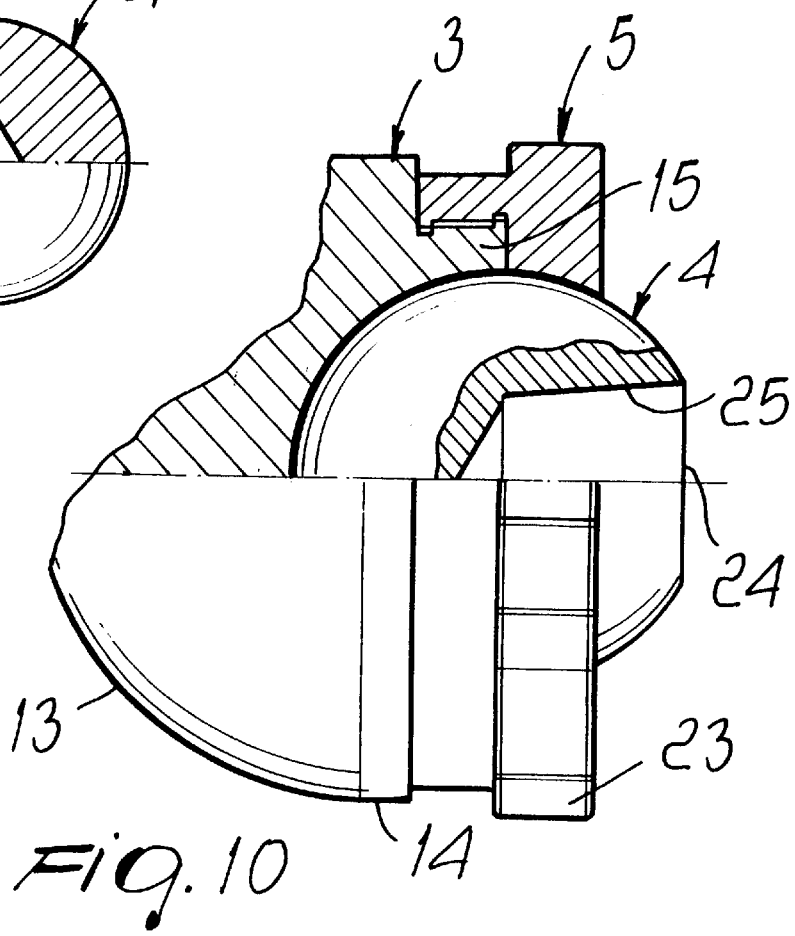
FIG. 10 is a partially cross-sectional view of part of the prosthesis according to a different embodiment.
Figure 11:
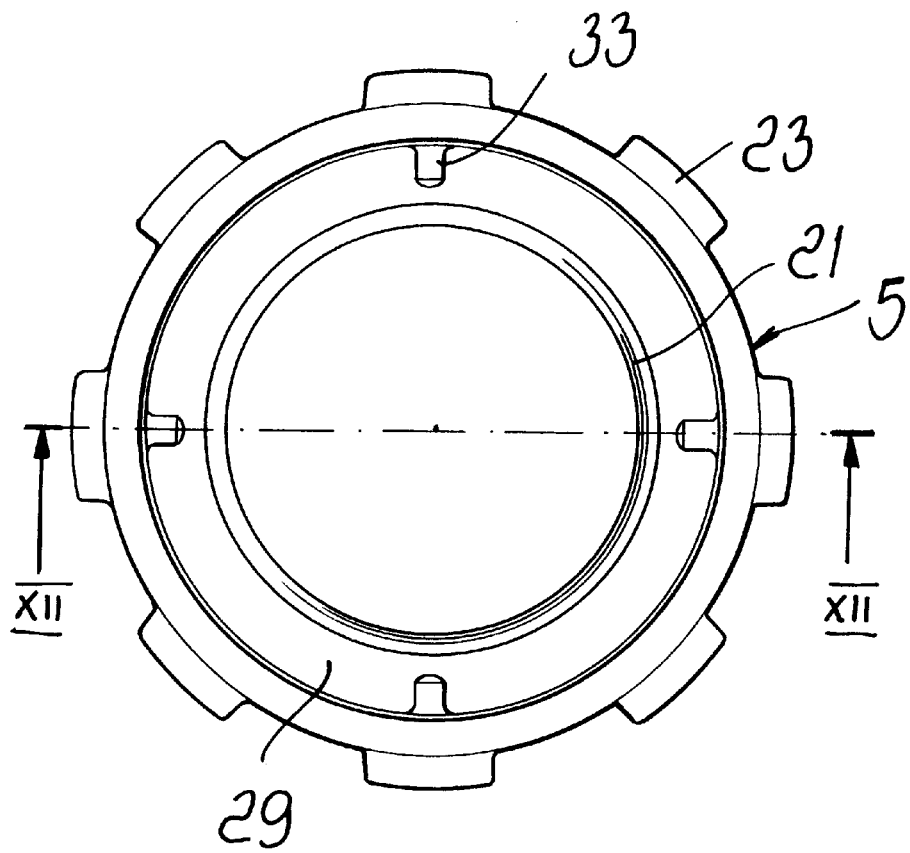
FIG. 11 is a view, taken from below or from the inside, of the flange according to the variation of FIG. 10.
Figure 12:
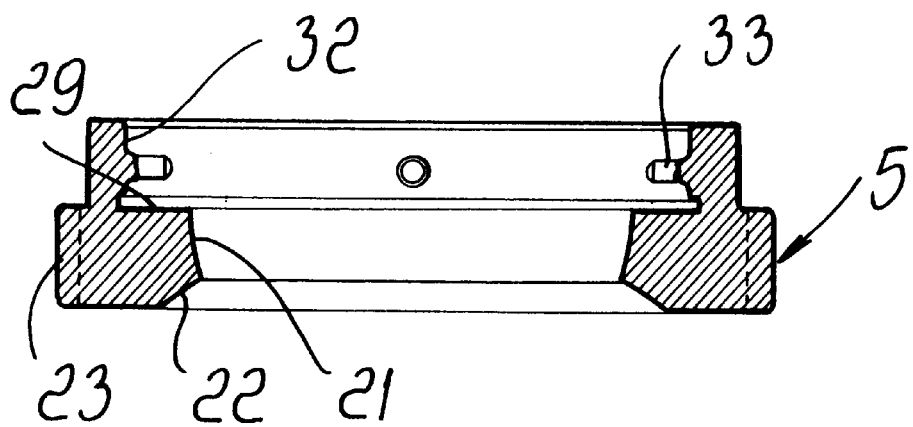
FIG. 12 is a cross-sectional view, taken along the line XII—XII of FIG. 11.
Figure 13:
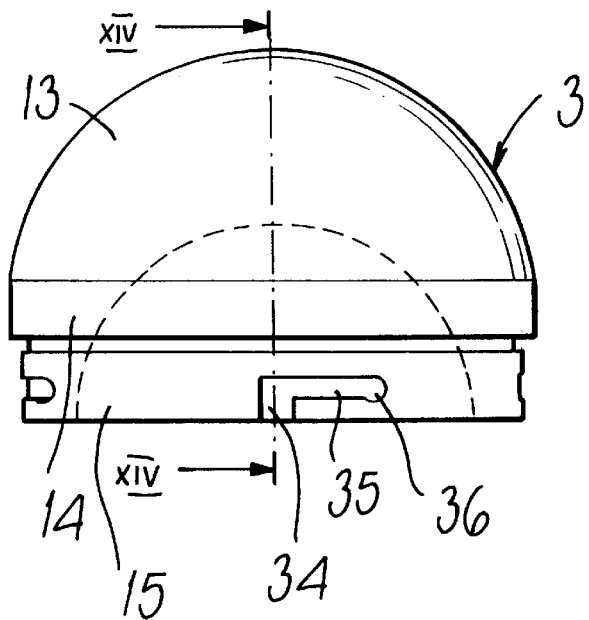
FIG. 13 is a view of a cotyloid cavity which can be coupled to the flange of FIGS. 11 and 12.
Figure 14:
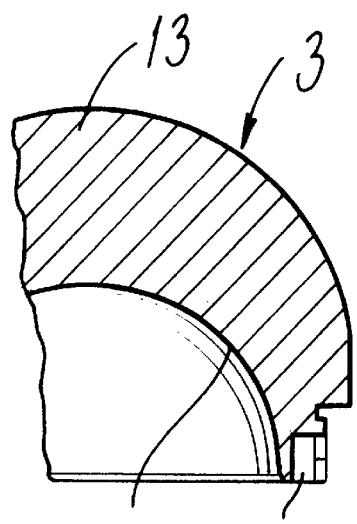
FIG. 14 is a partial cross-sectional view, taken along the line XIV—XIV of FIG. 13.
Figure 15:
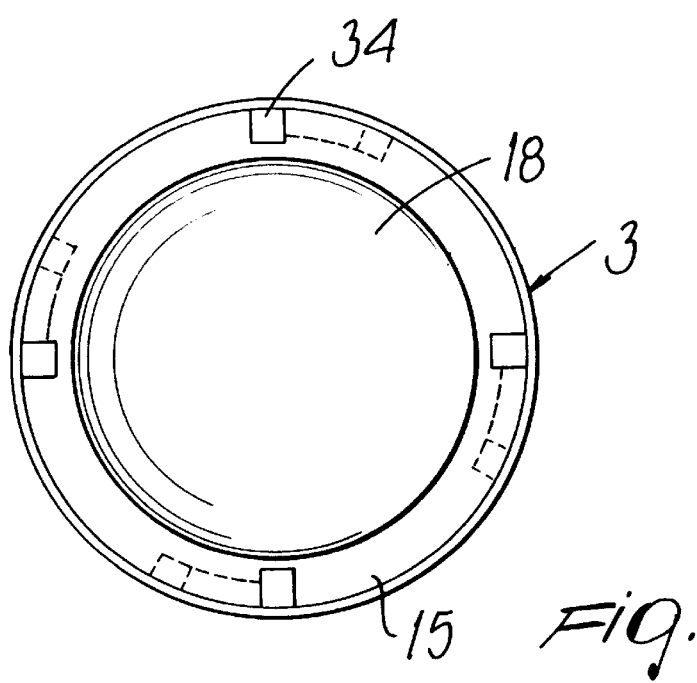
FIG. 15 is a view of the cotyloid cavity of FIG. 13, taken from below or from the concave region.

According to a different embodiment shown in FIG. 10, the flange 5 does not abut against the edge 12 of the ring 2, since its internally threaded portion 20 has a smaller diameter than the cylindrical portion 14 of the cotyloid cavity or insert.

It is possible to maintain the same cotyloid cavity 3 and the same flange 5, while modifying only tightening of the threaded portion, for various femoral heads 4; for example, head 4 can have a diameter of 22, 26, 28, 32 millimeters.

FIGS. 11 to 15 illustrate a different embodiment in which the cotyloid cavity 3 and the flange 5 are engaged by means of a snap-action device. As a matter of fact, the flange 5 is formed with a hole 32 which is designed to receive the cylindrical portion 14 of the cotyloid cavity 3. The hole 32 has a lateral surface having radial pins 33 which are angularly equidistant and to which respective seats formed in the outer surface of the cylindrical portion 14 of the cotyloid cavity correspond. Each seat is an axial slot 34 which can be entered frontally by the cylindrical portion 15 and is connected to a blind channel 35 which is substantially perpendicular thereto and terminates with a larger portion 36. During assembly, each pin 33 is placed in front of its respective slot 34. The axial approaching movement of the flange 5 towards the cotyloid cavity 3 causes each pin 33 to be seated in its respective slot 34 and a mutual rotation of the two components allows each pin 33 to slide along the channel 35 with a slight forcing due to the possible inclination of said channel; when the pin 33 snaps into place inside the larger portion 36, flange 5 is secured to the cotyloid cavity or insert 3.

The cotyloid cavity or insert 3 and the artificial femoral head 4 must have surfaces with an extremely accurate finish so as to allow them to move with minimum friction.

Ring 2 and the artificial femoral head 4 can be made of stainless steel, titanium or other material, while the cotyloid cavity or insert 3 and the flange 5 can be made of high-density polyethylene or of ceramic material.

The materials and the dimensions may be various according to requirements.

The invention is susceptible of numerous modifications and variations within the protective scope defined by the content of the appended claims.

The disclosures in Italian Utility Model Application No. VR98U000029 from which this application claims priority are incorporated herein by reference.

What is claimed is:

1. An, antiluxation hip prostheses having:
   a hollow ring nut, which can be secured to the pelvis and delimits a receiving seat;
   a cotyloid cavity or acetabular insert, which can be accommodated in said receiving seat and delimits substantially hemispherical acetabular seat or insert;
   a spherical head of an artificial femur which can be located in said seat of said cotyloid cavity; and
   a flange which can be inserted onto said artificial femur to abut against said spherical head and rigidly coupled to said cotyloid cavity to keep said spherical head permanently in said seat so that said spherical head is free to perform articulated movements therein, said flange having central hole with a concave radiused surface which, in use, engages said spherical head, and said flange and said cotyloid cavity being mutually coupleable through screw coupling.

2. A prosthesis according to claim 1, wherein said cotyloid cavity has a hemispherical dome part which terminates with a cylindrical portion which, in use, protrudes from said ring.

3. A prosthesis according to claim 1, wherein said flange has internal threads which are screwable about external threads provided on a cylindrical portion of said cotyloid cavity.

4. An antiluxation hip prosthesis having:
   a hollow ring nut, which can be secured to the pelvis and delimits a receiving seat;
   a cotyloid cavity or acetabular insert, which can be accommodated in said receiving seat and delimits a substantially hemispherical acetabular seat or insert;
   a spherical head of an artificial femur which can be located in said seat of said cotyloid cavity; and
   a flange which can inserted onto said artificial femur to abut against said spherical head and rigidly coupled to said cotyloid cavity to keep said spherical head permanently in said seat so that said spherical head is free to perform articulated movements therein, said flange having a central hole with a concave radiused surface which, in use, engages said spherical head, said flange and said cotyloid cavity being mutually coupleable through a bayonet coupling adapted to mutually couple said flange and said cotyloid cavity by means of an axial approaching movement and a mutual rotation movements between said flange and said cotyloid cavity.

5. A prosthesis according to claim 4, wherein said flange has at least two internal radial pins and wherein said cotyloid cavity has a seat arranged on a cylindrical portion of said cotyloid cavity for locating by snap action each pin of the flange.

6. A prosthesis according to claim 5, wherein each seat comprises an axial slot accessible from a front of said cylindrical portion and connected to a blind channel which is substantially perpendicular to said axial slot and terminates with a larger portion.

7. A prosthesis according to claim 1, wherein said flange has an external toothed ring for safe grip and easy handling during assembly and screwing onto said cotyloid cavity.

8. A prosthesis according to claim 4, wherein said flange has an external toothed ring for safe grip and easy handling during assembly and screwing onto said cotyloid cavity.

* * * * *